United States Patent [19] [11] Patent Number: 4,535,140
Schoenberg et al. [45] Date of Patent: Aug. 13, 1985

[54] HOT-MELT ADHESIVES BASED ON VINYL POLYMER

[75] Inventors: Jules E. Schoenberg, Scotch Plains; Thomas P. Flanagan, Green Brook; Dilip K. Ray-Chaudhuri, Bridgewater, all of N.J.

[73] Assignee: National Starch and Chemical Corporation, Bridgewater, N.J.

[21] Appl. No.: 284,162

[22] Filed: Jul. 17, 1981

[51] Int. Cl.$^3$ .................. C08F 210/14; C09J 00/00
[52] U.S. Cl. .................... 526/329; 156/327
[58] Field of Search ............. 526/329, 348.3

[56] References Cited

U.S. PATENT DOCUMENTS

| 2,970,974 | 2/1961 | Albus et al. | 260/27 |
| 3,052,657 | 9/1962 | Calhoun et al. | 526/348.3 |
| 3,541,188 | 11/1970 | Srail | 260/889 |
| 3,626,026 | 12/1971 | Fukumuru et al. | 260/857 |
| 3,630,980 | 12/1971 | Russell | 526/329 |
| 3,647,771 | 3/1972 | Nakaguchi et al. | 526/329 |
| 3,954,697 | 5/1976 | McConnell et al. | 526/348.3 |
| 3,991,025 | 11/1976 | Kutch et al. | 260/24 |
| 4,259,470 | 3/1981 | Trotter et al. | 526/348.3 |
| 4,264,756 | 4/1981 | Trotter et al. | 526/348.3 |

FOREIGN PATENT DOCUMENTS 1119045  7/1968  United Kingdom .

OTHER PUBLICATIONS

Flanagan, Handbook of Adhesive Bonding, Cagle, McGraw Hill, (1973), (Chap. 8–Hot-Melt Adhesives), p. 8-1.

Primary Examiner—Harry Wong, Jr.
Attorney, Agent, or Firm—Edwin M. Szala

[57] ABSTRACT

A hot-melt adhesive especially useful in the construction of disposable diapers contains a vinyl polymer of 40-90% by weight of a $C_1$-$C_{12}$ alkyl acrylate and 10-60% by weight of an alpha-olefin of $C_{20}$-$C_{40}$, wherein the alkyl acrylate may be partially replaced with vinyl acetate or with a $C_6$-$C_{12}$ olefin or with mixtures thereof, provided that the polymer contain at least 10% by weight of the alkyl acrylate. The adhesive may also contain a tackifying resin, a wax, an oil or a stabilizer depending on the specific end-use desired. In a preferred embodiment the polymer contains 20-45% by weight of the alpha-olefin.

9 Claims, No Drawings

HOT-MELT ADHESIVES BASED ON VINYL POLYMER

BACKGROUND OF THE INVENTION

This invention relates to a hot-melt adhesive based on vinyl polymer and to a process for adhering surfaces therewith.

Hot-melt adhesives are bonding agents which achieve a solid state and resultant strength by cooling, as contrasted with other adhesives which set or harden by chemical reaction or loss of solvent or water vehicle. Prior to heating the hot-melt adhesive is a thermoplastic material in the form of a 100% by weight solid. Application of heat melts the adhesive so that it can be readily applied to the substrate desired. After removal of heat, the adhesive returns to the solid state by simple cooling.

Combinations of polymers and copolymers containing polyethylene, rubbers and the like have been proposed in the past as the basic component of hot-melt adhesive compositions. Often such compositions include several ingredients additional to the base polymer to improve specific properties of the adhesive such as its viscosity in the molten state (melt viscosity), peel strength, flexibility, stability and the like.

The base polymer currently of choice for use in hot-melt adhesives designed to give good adhesion between polar and nonpolar surfaces is a copolymer of ethylene and vinyl acetate. Such polymers are produced by polymerizing ethylene and vinyl acetate at very high pressures of 15,000 to 40,000 psi (1055–2812 kg/cm$^2$) and at temperatures of from 150° to 250° C. A hydrocarbon wax is generally added to the copolymer thus obtained in amounts of 25 to 50% by weight of the total mixture to improve the hot-melt performance of the copolymer. Such waxes as are employed, however, have become increasingly costly and difficult to obtain due to the uncertainty in supply of petroleum available.

It is an object of the present invention to provide a novel hot-melt adhesive based on a polymer derived from higher alpha-olefins which requires no hydrocarbon wax yet performs comparably to commercially available hot-melt formulations.

It is another object to provide a process for adhering surfaces with such an adhesive.

SUMMARY OF THE INVENTION

The above and related objects are achieved in a novel hot-melt adhesive comprising a vinyl polymer comprising:
(a) 40–90% by weight of a $C_1$–$C_{12}$ alkyl acrylate and
(b) 10–60% by weight of an alpha-olefin of $C_{20}$–$C_{40}$, wherein said alkyl acrylate may be partially replaced with up to 60% by weight, based on the polymer, of vinyl acetate or with up to 10% by weight, based on the polymer, of $C_6$–$C_{12}$ olefin or with a mixture of vinyl acetate and $C_6$–$C_{12}$ olefin, provided that the polymer contain at least 10% by weight of said alkyl acrylate.

The adhesive may optionally contain a tackifying resin, wax, oil and/or stabilizer if desired.

DESCRIPTION OF THE PREFERRED EMBODIMENTS

The hot-melt adhesive of this invention is a vinyl polymer which is derived from at least two basic monomers, each in an amount within a given range. The alkyl acrylate monomer required to prepare the polymer generally comprises 40 to 90% by weight of the polymer. The choice of particular alkyl acrylate and amount thereof determines the character of the polymer and, thus, of the resulting adhesive. For example, methyl acrylate lends hardness and brittleness to the adhesive, ethyl acrylate results in tough rubbery polymers, and butyl and octyl acrylates in large amounts yield pressure-sensitive adhesives. The alkyl acrylate useful herein contains 1 to 12 carbon atoms in the alkyl portion, and preferably is ethyl or butyl acrylate.

The alpha-olefin monomer required in the basic vinyl polymer of the adhesive is a solid at room temperature and contains from 20 to 40 carbon atoms, preferably 20–30 carbon atoms. The olefin portion of the polymer retains its crystallinity in the polymer by side-chain crystallization and thus imparts cohesive strength to the adhesive. Thus, olefins of less than 20 carbon atoms are not useful herein since they tend to be liquids or cold-flowing solids under ambient conditions. The preferred olefins herein are those mixture of olefins such as the $C_{20}$–$C_{24}$ olefin mixture supplied by Gulf Oil Chemicals Company under the trademark Gulftene 20–24 prepared by Ziegler polymerization of ethylene and primarily composed of eicosene (49 weight percent), docosene (42 weight percent) and tetracosene (8 weight percent). Also preferred is the $C_{24}$–$C_{28}$ olefin mixture composed of 30% $C_{24}$ olefin, 39% $C_{26}$ olefin, 20% $C_{28}$ olefin and 10% $C_{30+}$ olefin sold under the trademark Gulftene 24–28. Another mixture which is useful herein is the $C_{30+}$ olefin mixture of 28% $C_{28}$ olefin and 78% $C_{30+}$ olefin sold under the trademark Gulftene 30+.

The amount of alpha-olefin monomer useful herein is 10–60%, and preferably 20–45% by weight of the polymer. If the amount of olefin is higher than about 60%, chain transfer occurs to a large degree with the result that the polymer is a wax-like material with an unsuitably low viscosity. If, on the other hand, the amount of olefin in the polymer is too low, the resulting adhesive will not have the requisite cohesive strength due to lack of crystallinity in the polymer.

In addition to the two required monomers mentioned above, the polymer may optionally be derived from additional monomers if desired. Thus, the alkyl acrylate monomer can be partially replaced with up to about 60% by weight, based on the polymer, of vinyl acetate or with up to 10% by weight, based on the polymer, of a $C_6$–$C_{12}$ olefin or mixtures thereof, provided that the polymer contain at least 10% by weight of alkyl acrylate. The amount of vinyl acetate to be added will depend on the degree of brittleness desired in the adhesive. The $C_6$–$C_{12}$ olefins, which are particularly preferred because they lend internal plasticity to the polymer, cannot be used in amounts of more than about 10% of the polymer due to their chain transfer properties. An especially preferred polymer for use as an adhesive herein is a terpolymer of 10–30% by weight alkyl acrylate, 30–60% by weight of vinyl acetate and 10–60% by weight of the alpha-olefin. Other monomers such as allyl esters or alpha-olefins of $C_3$–$C_{19}$ may be employed in amounts of up to 15% by weight to replace the alkyl acrylate monomer, if they do not adversely affect the desired properties of the hot-melt adhesive to a significant degree. Examples of unsuitable monomers herein are styrene and alkyl methacrylate, which tend to homopolymerize.

The polymers of this invention are prepared by free-radical-initiated polymerizations which are well known and described in the art. In a typical method of preparing the polymers, all of the olefin, a portion of the other monomers and the free-radical initiator (such as benzoyl peroxide or tert-butyl perbenzoate) are mixed together in a vessel and the mixture is heated to reflux with stirring. Thereafter, a mixture of the remaining amounts of vinyl acetate and alkyl acrylate is slowly added over about three hours. Heating is continued until the internal temperature reaches 150° C. (about three hours). A viscous polymer is formed and the antioxidant or stabilizer is added. The residual monomers if any are removed by vacuum distillation.

It is to be noted that a non-uniform polymer may lead to a useless adhesive which separates into two or more phases in the melt. In preparing uniform polymers it is desirable to consider the relative reactivities of the monomers, especially when olefins of molecular weight greater than a $C_{24}$ molecular weight are employed.

The preferred polymer herein has a viscosity in the range of 500 to 20,000 cps, but a viscosity outside this range is still within the scope of this invention if the hot-melt adhesive formulated from the polymer functions adequately.

While the vinyl polymers of the present invention are useful by themselves as adhesives without being modified in any way, it may be advantageous in certain applications to blend other components therewith. For example, tackifying resins may be incorporated into the hot-melt adhesive to alter or optimize the properties desired in the adhesive such as its bond strength and melt viscosity. The tackifier may also produce a reinforcing or plasticizing (flexibility) effect or contribute to stickiness (better molten tack) and particular wetting ability. Representative of suitable tackifying resins are, for example, the rosin and rosin esters (such as those available from Hercules Chemical Co. under the trademark FORAL), aromatic hydrocarbon resins including styrene polymers and copolymers (such as the low-molecular-weight polystyrene resins available from Hercules Chemical Co. under the trademarks PICCOLASTIC and KRISTALEX RESINS) and alphamethylstyrene/vinyl toluene resins (available from Hercules Chemical Co. under the trademark PICCOTEX), the coumarone-indene resins, aromatic-aliphatic copolymer resins, aromatic petroleum oils, phenolic resins, and the like. The tackifying resin, if employed, is typically present in amount of 5–25% by weight of the total adhesive.

Additionally, various other modifiers may be employed including stabilizers or antioxidants such as Irganox 1010, butylated hydroxy-toluene or alkyl aryl phosphite, plasticizers such as dioctyl phthlalate, pigments such as calcium carbonate, silicon dioxide, titanium dioxide and zinc oxide, oils such as white mineral oil and castor oil, and waxes such as paraffin, microcrystalline or synthetic waxes and equivalents thereof such a $C_{20}$–$C_{40}$ olefins. The waxes, which are preferably employed in amounts no greater than 25% by weight of the adhesive, function so as to reduce the melt viscosity or alter the cohesive or dryness characteristics without appreciably decreasing bond strength. Furthermore, addition of oil or wax tends to decrease adhesion of the polymer to give an adhesive with a removable peel strength as discussed hereinafter.

In the formation of the hot-melt adhesive, the various additives such as antioxidants, plasticizers and tackifying resins are generally added at the end of polymerization, either to the polymerization vessel (prior or subsequent to removing residual monomer) or to a separate mixing vessel; in some instances, however, one or more ingredients may be added in the beginning of the polymerization, providing, of course, that they do not detrimentally interfere with the polymerization. By way of illustration, plasticizer may be added at the beginning of polymerization and the antioxidants and tackifying resins added at the end thereof. In the typical procedure the formulations are prepared by remelting the vinyl polymer in a stainless steel beaker at about 150° C. and blending therewith the optional components with heating and stirring at a rate and timing such that lumping is avoided. Mixing and heating are continued until a smooth, homogeneous mass is obtained, whereupon the resultant hot-melt adhesive is drawn off. The adhesive thus obtained may be used immediately in hot pots or may be molten-extruded or converted into cylinders, slugs or billets depending on the physical character of the solid adhesive. If desired, the adhesive may be placed in cooling pans or drums and held in bulk for later use.

A particularly important area for utilization of the hot-melt adhesives of the present invention is in preparing disposable diapers. Thus, the adhesive is applied hot to one side of a polyethylene layer which is then joined to the cellulosic layer, and on cooling the layers adhere firmly. When the diaper is to be discarded, the layers are peeled apart, allowing separate disposal of the parts of the construction, a desirable feature when different means are advised for disposal of each part. The bond obtained in such application has high cohesive strength but is readily removable on demand. Depending on the application and the substrates employed, the adhesive may also be used to form a permanent bond between the layers which will not separate without tearing of the layers.

Other areas for utilization include the construction of disposable sanitary products such as sanitary napkins and other such applications wherein hot-melt adhesives of the character described herein would be useful.

The following examples illustrate the efficacy of the hot-melt adhesives herein. All parts and percentages are given by weight and all temperatures in degrees Centigrade unless otherwise noted.

The following test procedures were used to evaluate the polymers and hot-melt adhesive compositions of this invention:

MELT VISCOSITY TEST

The molten viscosities of the polymer and of the hot-melt adhesive at a given temperature (usually 120° to 150° C.) are measured in centipoises (cps) utilizing a Thermosel Viscometer as supplied by Brookfield Engineering of Stoughton, Mass. Thermal stability of the adhesive is determined by measuring the viscosity of the adhesive after aging for one week at 150° C.

PEEL STRENGTH (REMOVABLE BOND)

A molten film of the adhesive of 50 to 100 microns thickness is cast using a heated glass rod or Bird applicator on a Teflon (trademark) coated steel sheet and allowed to solidify. Strips of 0.65 cm width are cut from the film and inserted between pieces of polyethylene film and nonwoven cloth. A heat-sealing machine with a pressure of 1.4 kg/cm$^2$ and a temperature of 135° C. is applied to the lamination for three seconds to form the bond. Peel strength is tested by peeling the polyethylene film from the nonwoven using an Instron Tensile Tester with a separation rate of 5.1 cm per minute. The peel strength is measured in gram units and is in the range of 15-40 g for best results.

PEEL STRENTH (PERMANENT BOND)

The hot-melt adhesive is applied as a bead onto polyethylene film at 93° to 107° C. in a stream of about 1.6 mm diameter flowing from a glass rod. The adhesive bead is immediately chilled by a water spray to avoid distortion of the polyethylene film. The bead on the polyethylene is bonded to nonwoven paper by rolling over the combined substrates with a 2 kg rubber-coated roller. The bond is tested by peeling the substrates apart either slowly by hand or on an Instron Tensile Tester with a separation rate of 5.1 cm per minute. A permanent bond produces a tear in the nonwoven paper when separated.

EXAMPLE I

A one-liter round-bottom flask was charged with 150 g of $C_{20}$-$C_{24}$ olefin sold under the trademark Gulftene 20-24, 90 g of vinyl acetate, 1.5 g of ethyl acrylate, 2.5 g of tert-butyl perbenzoate and 10 g of a 50% mixture of benzoyl peroxide and dicyclohexyl phthalate. The mixture was heated to reflux with stirring and a solution containing 210 g of vinyl acetate and 48.5 g of ethyl acrylate was added over a three-hour period. The boiling point of the mixture remained between 80° and 86° C. during the addition. Heating was continued until the internal temperature reached 150° C. (three hours). One gram of Irganox 1010 (antioxidant) was then added and the unreacted monomer (2.7%) removed by vacuum distillation. A terpolymer (Polymer I) was thereby produced.

Polymer II was prepared in an indentical manner except that butyl acrylate was substitued for ethyl acrylate.

Adhesives A-D in Table I were prepared by mixing either Polymer I or Polymer II with the indicated ingredients in the given amounts at 150° C. until a homogeneous mass was obtained. The properties of the polymers and the adhesives are given in Table I.

TABLE I

| Ingredients (parts): | Adhesive | | | |
|---|---|---|---|---|
| | A | B | C | D |
| Polymer I (containing 30% olefin, 60% vinyl acetate and 10% ethyl acrylate) | 75 | 75 | 75 | — |
| Polymer II (containing 30% olefin, 60% vinyl acetate and 10% butyl acrylate) | — | — | — | 75 |
| Paraffin wax | 25 | 20 | — | 5 |
| White mineral oil | — | 5 | — | 20 |

TABLE I-continued

| Ingredients (parts): | Adhesive | | | |
|---|---|---|---|---|
| | A | B | C | D |
| Polystyrene of softening point 25 (sold by Hercules under the trademark Piccolastic A 25) | — | — | 25 | — |
| Properties: | | | | |
| Melt Viscosity of Polymer at 150° C. (cps) | 3875 | 3875 | 3875 | 3500 |
| Melt Viscosity of Adhesive at 120° C. (cps) | 2900 | 2875 | 2920 | 2690 |
| Melt Viscosity of Adhesive at 120° C. after one week aging at 150° C. (cps) | * | 3000 | * | 2875 |
| Peel Strength (Removable) (g) | 20 | 25 | 30 | 35 |

*Not determined.

It is seen that the removable peel strengths for all four adhesives were comparable to the peel strength of 24-32 g obtained on testing a commercial diaper of Procter & Gamble Co. bonded with a commercially available hot-melt adhesive used as a comparison. Furthermore, the melt viscosity of each adhesive is desirably reduced as compared with the melt viscosity of the base polymer alone.

EXAMPLE II

The procedure of Example I was used to prepare Polymers III-V employing the ingredients given below in the indicated amounts:

| Ingredients for Polymerization (parts): | Polymers | | |
|---|---|---|---|
| | III | IV | V |
| Initial Charge: | | | |
| $C_{24}$-$C_{28}$ olefin | 30 | 20 | 40 |
| 1-decene | 5 | 10 | — |
| vinyl acetate | 9 | 12 | 12 |
| ethyl acrylate | 1 | — | — |
| butyl acrylate | — | 1 | 0.6 |
| 50% mixture of benzoyl peroxide and dicyclohexyl phthalate | 0.1 | 0.4 | 1.0 |
| t-butyl perbenzoate | 0.5 | 0.5 | 0.5 |
| Slow Add: | | | |
| Vinyl acetate | 21 | 28 | 28 |
| Ethyl acrylate | 34 | — | — |
| Butyl acrylate | — | 29 | 19.4 |
| 50% mixture of benzoyl peroxide and dicyclohexyl phthalate | 0.5 | 0.4 | 1.0 |
| Melt Viscosity of Polymer at 150° C. (cps): | 1440 | 1000 | 800 (at 120° C.) |

The composition and properties of the Adhesives E-G prepared from Polymers III-V, respectively, are given in Table II.

| | Adhesives | | |
|---|---|---|---|
| | E | F | G |
| Ingredients (parts): | | | |
| Polymer III (tetrapolymer containing 30% olefin, 30% vinyl acetate, 35% ethyl acrylate and 5% decene) | 90 | — | — |
| Polymer IV (tetrapolymer containing 20% olefin, 40% vinyl acetate, 30% butyl acrylate and 10% decene) | — | 90 | — |
| Polymer V (terpolymer containing 40% olefin, 40% vinyl acetate and 20% butyl acrylate) | — | — | 100 |
| Alphamethyl styrene/styrene copolymer (sold by Hercules under the trademark KRISTALEX 85) | 10 | — | — |
| Microcrystalline wax (m.p. 195° C.) | — | 10 | — |

-continued

| | Adhesives | | |
|---|---|---|---|
| | E | F | G |
| Alkyl aryl phosphite (stabilizer) | — | 0.25 | — |
| Properties: | | | |
| Melt Viscosity of Adhesive at 150° C. (cps) | 940 | 1440 | 800 (at 120° C.) |
| Peel Strength (permanent) | 100% tear | * | * |
| Peel Strength (removable) (g) | * | 20 | 30 |

*Not appropriate

The results indicate that tetrapolymers are also effective in formulating a suitable hot-melt adhesive for permanent and removable bonds. In addition, it is seen that the polymer can be employed as an adhesive as 100% material.

EXAMPLE III

Polymer VI (copolymer containing 30% olefin and 70% ethyl acrylate) was prepared by charging a 500-ml round-bottom flask with 75 g of $C_{20}$–$C_{24}$ olefin of Example I, 9 g of ethyl acrylate and 1.5 g of t-butyl perbenzoate. The solution was heated to 115° C. under a nitrogen atmosphere and 166 g of ethyl acrylate was added over a two-hour period while maintaining a temperature around 115° C. The reaction mixture was heated for one hour at 130° C. Then 0.5 g of Irganox 1010 (trademark) was added and the volatile materials (0.3%) were removed by vacuum distillation. The viscosity of the polymer was 1810 cps at 150° C.

An adhesive formulation prepared with 90 parts of Polymer VI and 10 parts of alpha-methyl styrene/styrene copolymer had the following properties:

| Melt Viscosity at 150° C.: | 1575 cps |
|---|---|
| Melt Viscosity of Adhesive at 150° C. after 3 days aging at 150° C.: | 1450 cps |
| Peel Strength (Removable): | 34 g |

EXAMPLE IV (Comparative)

Polymer VII was prepared by the method described in Example I employing the following ingredients:

| Initial charge: | Parts |
|---|---|
| 1-hexadecene | 25 |
| vinyl acetate | 18 |
| ethyl acrylate | 0.5 |
| 50% mixture of benzoyl peroxide and dicyclohexyl phthalate | 2.5 |
| t-butyl perbenzoate | 2.5 |
| Slow addition: | |
| vinyl acetate | 42 |
| ethyl acrylate | 14.5 |
| 50% mixture of benzoyl peroxide and dicyclohexyl phthalate | 2.5 |

The terpolymer thus obtained (containing 25% olefin, 60% vinyl acetate and 15% ethyl acrylate) has a melt viscosity at 120° C. of 6050 cps and was ineffective as an adhesive due to its relative weakness and cold-flowing properties.

In summary, the present invention provides a hot-melt adhesive containing a vinyl polymer derived from higher alpha-olefins requiring no wax for its good performance.

Now that the preferred embodiments of the invention have been described in detail, various modifications and improvements thereon will become readily apparent to the practitioner. Accordingly, the spirit and scope of the present invention are to be limited only by the appended claims, and not by the foregoing specification.

What is claimed is:

1. A solvent-free 100 percent solid vinyl polymer hot melt adhesive comprising:
   (a) 10–90% by weight of a $C_1$–$C_{12}$ alkyl acrylate and
   (b) 10–60% by weight of an alpha-olefin of $C_{20}$–$C_{40}$, wherein said alkyl acrylate is partially replaced with up to 60% by weight, based on the polymer, of vinyl acetate or with up to 10% by weight, based on the polymer, of a $C_6$–$C_{12}$ olefin or with a mixture of vinyl acetate and $C_6$–$C_{12}$ olefin, provided that the polymer in all instances contains at least 10% by weight of said alkyl acrylate.

2. The adhesive of claim 1 wherein said alpha-olefin is present in an amount of 20–45% by weight of the polymer.

3. The adhesive of claim 1 wherein said alpha-olefin is of $C_{20}$–$C_{30}$.

4. The adhesive of claim 1 wherein said adhesive comprises 10–30% by weight of said alkyl acrylate, 30–60% by weight of said vinyl acetate and 10–60% by weight of said alpha-olefin.

5. The adhesive of claim 1 wherein said alkyl acrylate is ethyl or butyl acrylate.

6. A solvent-free 100 percent solid vinyl polymer hot melt adhesive comprising:
   (a) 40–90% by weight of a $C_1$–$C_{12}$ alkyl acrylate and
   (b) 10–60% by weight of an alpha-olefin of $C_{20}$–$C_{40}$.

7. The adhesive of claim 6 wherein said alpha-olefin is present in an amount of 20–45% by weight of the polymer and is of $C_{20}$–$C_{30}$, and said alkyl acrylate is ethyl or butyl acrylate.

8. A solvent-free 100 percent solid vinyl polymer hot melt adhesive prepared by polymerizing:
   (a) 10–90% by weight of a $C_1$–$C_{12}$ alkyl acrylate and
   (b) 10–60% by weight of an alpha-olefin of $C_{20}$–$C_{40}$, wherein said alkyl acrylate is partially replaced with up to 60% by weight, based on the polymer, of vinyl acetate or with up to 10% by weight, based on the polymer, of a $C_6$–$C_{12}$ olefin or with a mixture of vinyl acetate and $C_6$–$C_{12}$ olefin, provided that the polymer in all instances contains at least 10% by weight of said alkyl acrylate, in the presence of
   (c) a free-radical initiator and in the absence of any solvent, and recovering said adhesive as a 100 percent solid adhesive.

9. A solvent-free 100 percent solid vinyl polymer hot melt adhesive prepared by polymerizing:
   (a) 40–90% by weight of a $C_1$–$C_{12}$ alkyl acrylate and
   (b) 10–60% by weight of an alpha-olefin of $C_{20}$–$C_{40}$ in the presence of
   (c) a free-radical initiator and
   in the absence of any solvent, and recovering said adhesive as a 100 percent solid adhesive.

* * * * *